United States Patent
Isab et al.

(10) Patent No.: US 9,561,237 B1
(45) Date of Patent: Feb. 7, 2017

(54) BIS-(TRIETHYLPHOSPHINE)PLATINUM(II) COMPLEXES WITH THIONES AS ANTI CANCER AGENTS

(71) Applicant: KING FAHD UNIVERSITY OF PETROLEUM AND MINERALS, Dhahran (SA)

(72) Inventors: Anvar Husain Abdul Kadir Isab, Dhahran (SA); Muhammad Altaf, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/008,889

(22) Filed: Jan. 28, 2016

(51) Int. Cl.
*A61K 31/282* (2006.01)
*A61K 31/555* (2006.01)
*C07F 15/00* (2006.01)

(52) U.S. Cl.
CPC ......... *A61K 31/555* (2013.01); *C07F 15/0093* (2013.01)

(58) Field of Classification Search
USPC ............................ 514/184, 218, 254.02, 492
See application file for complete search history.

(56) References Cited

U.S. PATENT DOCUMENTS 9,481,699 B1 * 11/2016 Altaf .................. C07F 15/0093

FOREIGN PATENT DOCUMENTS

CN 102234295 B 1/2014

OTHER PUBLICATIONS

Rasul: International Journal of Oncology 40; 1153-1161, 2012.*
A. Zainelabdeen A. Mustafa, et al., "Tetrakis(1-3-diazinane-2-thione)platinum(II) chloride monohydrate complex: Synthesis, spectroscopic characterization, crystal structure and in vitro cytotoxic activity against A549, MCF7, HCT15 and HeLa human cancer lines", Inorganic Chemistry Communications, vol. 44, (2014), pp. 159-163.
Jianxin Lin, et al., "Synthesis and characterization of platinum(II) complexes with 2-imidazolidinethione, X-ray crystal structure of tetra(2-imidazolidinethione-S)platinum(II) iodide dimethylsulfoxide solvate monohydrate", Journal of Coordination Chemistry, vol. 61, No. 15, Aug. 10, 2008, pp. 2457-2469.

* cited by examiner

*Primary Examiner* — Pancham Bakshi
(74) *Attorney, Agent, or Firm* — Oblon, McClelland, Maier & Neustadt, L.L.P.

(57) ABSTRACT

Platinum(II) complexes having mixed ligands as anticancer agents. The central platinum atom is coordinated by two phosphine ligands and two heterocyclic thione ligands. Each heterocyclic thione ligand has a five-, six- or seven-membered heterocyclic ring with two nitrogen atoms at positions 1 and 3 of the ring and a thiocarbonyl group at position 2. Pharmaceutical compositions incorporated the platinum(II) complexes, methods of synthesizing the complexes and methods of treating cancers with the complexes or pharmaceutical compositions thereof are also described.

16 Claims, 4 Drawing Sheets

BIS-(TRIETHYLPHOSPHINE)PLATINUM(II) COMPLEXES WITH THIONES AS ANTI CANCER AGENTS

TECHNICAL FIELD

The present invention relates to complexes of a central Pt(II) atom coordinated to different ligands. Specifically, the present invention relates to Pt(II) complexes having phosphine-based and heterocyclic thione ligands, and includes the use of these Pt(II) complexes for treatment of cancers and cell proliferative disorders.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The cis-diaminedichlorido platinum(II) complex cis-[$(NH_3)_2PtCl_2$] is one of the most successful anticancer drugs for treating many types of solid tumors [A. S. Abu-Surrah and M. Kettunen, Current Medicinal Chemistry, 13(2006) 1337-1357—incorporated herein by reference in its entirety]. Clinically called cisplatin, this Pt(II) complex was first synthesized by Beyrone in 1844, but its biological activity was accidentally discovered by Rosenberg in 1965. Until today, cisplatin remains the most common drug for treating specific cancer cells including lung, ovarian, testicular, head, neck and bladder tumors. The major mechanism of action of cisplatin undergoes intracellular activation by replacing one or both chloride groups, then covalently binds to DNA forming Pt-DNA adduct and distort the DNA structurally to prevent replication. The downstream effects of replication inhibitory ultimately lead to cell death [T. C. Johnstone, G. Y. Park, and S. J. Lippard, Anticancer Res., 34 (2014) 471-476—incorporated herein by reference in its entirety].

Despite its worldwide success as an anticancer drug, cisplatin is not universally effective against some of the most common tumors, such as colon and breast tumors [J. Reedijk, Chem. Rev., 99 (1999) 499-2510—incorporated herein by reference in its entirety]. In addition, cisplatin therapy has several severe toxic side effects (e.g. nephrotoxicity, ototoxicity, neurotoxicity and emetogenesis). The common use of this drug has resulted resistance to the drug [L. Fuks, E. Anuszewska, H. Kruszewska, A. Krowczynski, J. Dudek, N. Sadlej-Sosnowska, Transition Met Chem, 35 (2010) 639-647; L. Giovagnini, L. Ronconi, D. Aldinucci, D. Lorenzon, S. Sitran, D. Fregona. J. Med. Chem., 48 (2005) 1588-1595—each incorporated herein by reference in its entirety]. It is postulated that nephrotoxicity poses the greatest challenge for cancer treatment with cisplatin [D. Kovala-Demertzi, P. N. Yadav, M. A. Demertzis, M. Coluccia. J. Inorg. Biochem., 78 (2000) 347-754—incorporated herein by reference in its entirety]. Due to its extreme drawbacks, efforts are being made to prepare new platinum (II) compounds to exhibit either higher cytotoxicity or reduced toxicity in comparison with cisplatin [A. G. Quiroga, J. M. Pe'rez, I. Lopez-Solera, J. R. Masaguer, A. Luque, P. Roman, A. Edwards, C. Alonso, C. Navarro-Ranninger, J. Med. Chem., 41(1998) 1399-1408—incorporated herein by reference in its entirety].

Pt(II) is a soft acid and its reactivity can be related according to the hard-soft acid-base theory. Pt(II) has a high affinity for sulfur-containing ligands, such as, thiosemicarbazones, dithiocarbamates, and xanthate [W. Friebolin, G. Schilling, M. Zoller, E. Amtmann. J. Med. Chem., 47 (2004) 2256-2263; J. Lin, G. Lu, L. M. Daniels, X. Wei, J. B. Sapp and Y. Deng, J. Coord. Chem., 61(2008) 2457-2469; Z. Ma, L. Rao, and U. Bierbach, J. Med. Chem., 52 (2009) 3424; J. M. Brow, C. R. Pleatman, and U. Bierbach, Bioorg. Med. Chem. Lett., 12 (2002) 2953—each incorporated herein by reference in its entirety].

Sulfur-containing ligands have been used for a long time as antifungal agents, rescue agents against nephritic side effects during cisplatin administration, and as inhibitors of HIV-1 and HIV-2 reverse transcriptases [R. del Campo, J. J. Criado, E. Garcia, M. A. R. Hermosa, A. Jiménez-Sánchez, J. L. Manzano, E. Monte, E. Rodríguez-Fernández, and F. Sanz, J. Biol. Inorg. Chem., 89 (2002) 74; J. Ren, J. Diprose, J. Warren, R. M. Esnouf, L. E. Bird, S. Ikemizu, M. Slater, J. Milton, J. Balzarini, D. I. Stuart, and D. K. Stammers, J. Biol. Chem., 275 (2000) 5633—each incorporated herein by reference in its entirety]. Pt(II) complexes with thiourea ligands demonstrated a different binding mechanism to DNA than that of cisplatin and showed excellent cytotoxicity against ovarian and leukemia cancer cell lines [Z. Ma, L. Rao, and U. Bierbach, J. Med. Chem., 52 (2009) 3424; J. M. Brow, C. R. Pleatman, and U. Bierbach, Bioorg. Med. Chem. Lett., 12 (2002) 2953—each incorporated herein by reference in its entirety].

To this end, Pt(II) complexes having thiourea ligands and their derivatives have been synthesized. Among such complexes is tetrakis(1-3-diazinane-2-thione)platinum(II) chloride monohydrate [A. Z. A. Mustafa, M. Altaf, M. Monim-ul-Mehboob, M. Fettouhi, M. I. M. Wazeer, A. A. Isab, V. Dhuna, G. Bhatia, K. Dhuna, Inorg. Chem. Commun., 44 (2014) 159-163—incorporated herein by reference in its entirety]. Tetra(2-imidazolidinethione-S)platinum(II) chloride was synthesized, characterized and the crystal structure of the complex was obtained [J. Lin, G. Lu. L. M. Daniels, X. Wei, J. B. Sapp, Y. Deng, J. Coord. Chem., 61(2008) 2457-2469—incorporated herein by reference in its entirety.

In view of the foregoing, and as part of the continuing efforts, the present disclosure describes Pt(II) complexes having thiourea derivatives ligands and exhibit efficacy against a variety of cancers but also lack the severe toxic side effects associated with conventional platinum-based drugs.

BRIEF SUMMARY OF THE INVENTION

According to a first aspect, the present disclosure provides a platinum(II) complex represented by Formula I, Formula II, Formula III, Formula IV, Formula V or Formula VI:

Formula I

Formula II

Formula III

Formula IV

Formula V

Formula VI or a pharmaceutically acceptable salt, tautomer, ester, solvate or prodrug thereof. $R_1$-$R_{18}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group.

In one or more embodiments, the platinum(II) complex is represented by Formula I, Formula III or Formula V.

In one or more embodiments, $R_1$-$R_{18}$ are each independently a hydrogen, a halogen, an optionally substituted $C_1$-$C_2$ alkyl group, an optionally substituted $C_1$-$C_2$ alkoxy group, an optionally substituted $C_2$ alkenyl group or an optionally substituted $C_2$ alkynyl group.

In one or more embodiments, $R_1$-$R_6$ are each an ethyl group; $R_7$-$R_{10}$ are each a hydrogen, a methyl group or an ethyl group; and $R_{11}$-$R_{18}$ are each a hydrogen.

In certain embodiments, the platinum(II) complex is one of the following:
cis-bis(triethylphosphine)di(imidazolidine-2-thione)platinum(II);
cis-bis(triethylphosphine)di(1-methylimidazolidine-2-thione)platinum(II);
cis-bis(triethylphosphine)di(1,3-dimethylimidazolidine-2-thione)platinum(II);
cis-bis(triethylphosphine)di(1,3-diethylimidazolidine-2-thione)platinum(II);
cis-bis(triethylphosphine)di(imidazolidine-2-thione)platinum(II);
cis-bis(triethylphosphine)di(tetrahydropyrimidine-2(1H)-thione)platinum(II);
cis-bis(triethylphosphine)di(1-methyltetrahydropyrimidine-2(1H)-thione)platinum(II); and
cis-bis(triethylphosphine)di(1,3-diazepane-thione)platinum(II).

In at least one embodiment, the platinum(II) complex further comprises one or more pharmaceutically acceptable anions.

In one embodiment, the one or more pharmaceutically acceptable anions are chloride.

According to a second aspect, the present disclosure provides a pharmaceutical composition comprising the platinum(II) complex of claim 1 or a pharmaceutically acceptable salt, tautomer, ester, solvate or prodrug thereof; and one or more pharmaceutically acceptable carriers, other active pharmaceutical agents non-active ingredients. The pharmaceutical composition, which can exist in solid, semi-solid or liquid dosage forms, is formulated for multiple modes of dosage.

According to a third aspect, the present disclosure provides a method for cancer treatment using the pharmaceutical composition incorporating the platinum(II) complex.

According to a fourth aspect, the present disclosure provide a method for inducing apoptosis in a cancer cell by contacting the cancer cell with the platinum(II) complex.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Referring now to the drawings, wherein like reference numerals designate identical or corresponding parts throughout the several views.

The present disclosure will be better understood with reference to the following definitions:

As used herein, "compound" and "complex" are used interchangeably, and are intended to refer to a chemical entity, whether in the solid, liquid or gaseous phase, and whether in a crude mixture or purified and isolated.

The term "alkyl", as used herein, unless otherwise specified, refers to a saturated straight, branched, or cyclic, primary, secondary, or tertiary hydrocarbon of typically $C_1$ to $C_8$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, thioalkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to ($C_2$-$C_{12}$)alkenyl groups, such as vinyl, allyl, butenyl, pentenyl, hexenyl, butadienyl, pentadienyl, hexadienyl, 2-ethyl hexenyl, 2-propyl-2-butenyl, 4-(2-methyl-3-ethenyl)-pentenyl. An alkenyl group can be unsubstituted or substituted with one or more suitable substituents.

The term "alkynyl" means a monovalent, unbranched or branched hydrocarbon chain having one or more triple bonds therein. The triple bond of an alkynyl group can be unconjugated or conjugated to another unsaturated group. Suitable alkynyl groups include, but are not limited to ($C_2$-$C_{12}$)alkynyl groups, such as ethynyl, propynyl, butyryl, pentynyl, hexynyl, 2-ethylhexynyl, 2-propyl-2-butyryl, 4-(2-methyl-3-ethynyl)-pentynyl. An alkynyl group can be unsubstituted or substituted with one or more suitable substituents.

When a substituent is noted as "optionally substituted", the substituents are selected from, for example, substituents, such as, halo, hydroxy, alkoxy, oxo, alkanoyl, alkanoyloxy, amino, alkylamino, disubstituted amines in which the 2 amino substituents are alkyl; alkanoylamino, substituted alkanoylaminothiol, alkylthio, alkylthiono, alkylsulfonyl, arylsulfonyl, sulfonamido, e.g., —$SO_2NH_2$, substituted sulfonamido, nitro, cyano, carboxy, carbamyl, e.g., —$CONH_2$, substituted carbamyl e.g., —CONHalkyl, —CONHaryl, —CONHarylalkyl or cases where there are two substituents on the nitrogen selected from alkyl; alkoxycarbonyl, guanidine, and the like.

As used herein, "analogue" refers to a chemical compound that is structurally similar to a parent compound, but differs slightly in composition (e.g., one atom or functional group is different, added, or removed). The analogue may or may not have different chemical or physical properties than the original compound and may or may not have improved biological and/or chemical activity. For example, the analogue may be more hydrophilic or it may have altered reactivity as compared to the parent compound. The analogue may mimic the chemical and/or biologically activity of the parent compound (i.e., it may have similar or identical activity), or, in some cases, may have increased or decreased activity. The analogue may be a naturally or non-naturally occurring variant of the original compound. Other types of analogues include isomers (enantiomers, diastereomers, and the like) and other types of chiral variants of a compound, as well as structural isomers.

As used herein, "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). The term "derivative" also includes conjugates, and prodrugs of a parent compound (i.e., chemically modified derivatives which can be converted into the original compound under physiological conditions).

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis [Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, *Curr. Pharm. Design.* 5(4):265-287; Pauletti et al. (1997). Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics, *Pharm. Biotech.* 11:345-365; Gaignault et al. (1996). Designing Prodrugs and Bioprecursors I. Carrier Prodrugs, *Pract. Med. Chem.* 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, *Eur. J. Drug Metab. Pharmacokinet.,* 15(2): 143-53; Balimane and Sinko (1999). Involvement of multiple transporters in the oral absorption of nucleoside analogues, *Adv. Drug Delivery Rev.,* 39(1-3):183-209; Browne (1997). Fosphenyloin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) Design of Prodrugs, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Methods Enzymol.* 112: 360-81; Farquhar D, et al. (1983). Biologically Reversible Phosphate-Protective Groups, *J. Pharm. Sci.,* 72(3): 324-325; Han, H. K. et al. (2000). Targeted prodrug design to optimize drug delivery, *AAPS PharmSci.,* 2(1): E6; Sadzuka Y. (2000). Effective prodrug liposome and conversion to active metabolite, *Curr. Drug Metab.,* 1(1):31-48; D. M. Lambert (2000) Rationale and applications of lipids as prodrug carriers, *Eur. J. Pharm. Sci.,* 11 Suppl 2:S15-27; Wang, W. et al. (1999) Prodrug approaches to the improved delivery of peptide drugs. *Curr. Pharm. Des.,* 5(4):265-87— each incorporated herein by reference in its entirety]. In some embodiments, "Pharmaceutically acceptable prodrugs" refer to a compound that is metabolized, for example hydrolyzed or oxidized, in the host to form the pharmaceutical composition of the present disclosure. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The term "tautomer", as used herein, refers to a constitutional isomer of a compound of this disclosure, specifically the one or more thione-based heterocyclic ligands coordinated to the platinum core atom, that readily interconvert between a thione form having a saturated heterocyclic ring and a thiol form having a non-saturated heterocyclic ring by a chemical reaction called tautomerization. The tautomerization chemical reaction results in the formal migration of a hydrogen atom or proton, which is accompanied by a switch of a single bond and an adjacent double bond in a thiocarbonyl group or in the heterocyclic ring. It should be understood that all tautomeric forms, which share the same molecular formula and insofar as they may exist, are included within the invention. It should also be appreciated that these tautomers can exist in equilibrium.

The term "therapeutically effective amount" as used herein refers to that amount of the compound being administered which will relieve to some extent one or more of the symptoms of the disorder being treated. In reference to cancer or pathologies related to increased cell division, a therapeutically effective amount refers to that amount which has the effect of at least one of the following: (1) reducing the size of a tumor, (2) inhibiting (that is, slowing to some extent, preferably stopping) aberrant cell division, growth or proliferation, for example cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer and (5) inducing apoptosis of cancer cells or tumor cells.

As used herein, the terms "therapies" and "therapy" can refer to any method(s), composition(s), and/or agent(s) that can be used in the prevention, treatment and/or management of a cancer or one or more symptoms thereof.

As used herein, the terms "treat," "treatment," and "treating" in the context of the administration of a therapy to a subject in need thereof refer to the reduction or inhibition of the progression and/or duration of cancer, the reduction or amelioration of the severity of cancer, and/or the amelioration of one or more symptoms thereof resulting from the administration of one or more therapies. In some embodiments, the subject is a mammalian subject. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with a cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to a stabilization or reduction in the cancer stem cell population. In some embodiments, such terms refer to a stabilization or reduction in the growth of cancer cells. In some embodiments, such terms refer to stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the pharmaceutical composition refers to the combination of an active agent with a carrier, inert or active, making the composition especially suitable for diagnostic or therapeutic use in vivo or ex vivo.

"Pharmaceutically acceptable salt" or "pharmaceutically acceptable ester" refers to a compound in a pharmaceutically acceptable form such as an ester, a phosphate ester, a salt of an ester or a related) which, upon administration to a subject in need thereof, provides at least one of the platinum(II) complexes described herein. Pharmaceutically acceptable salts and ester retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Suitable salts include those derived from alkali metals such as potassium and sodium, alkaline earth metals such as calcium and magnesium, among numerous other acids well known in the art.

A "pharmaceutical composition" refers to a mixture of the compounds described herein or pharmaceutically acceptable salts, esters or prodrugs thereof, with other chemical components, such as physiologically and pharmaceutically acceptable carriers, diluents and excipients. One purpose of a pharmaceutical composition is to facilitate administration of at least one platinum(II) complex to a subject.

As used herein, a "pharmaceutically acceptable carrier" or "pharmaceutically acceptable excipient" refers to a carrier or diluent that does not cause significant irritation to an organism and does not abrogate the biological activity and properties of the administered platinum(II) complex. The term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

As used herein, a "binder" holds the ingredients in a tablet together. Binders ensure that tablets and granules can be formed with required mechanical strength, and give volume to low active dose tablets. Binders may be: (1) saccharides and their derivatives, such as sucrose, lactose, starches, cellulose or modified cellulose such as microcrystalline cellulose, carboxymethyl cellulose, and cellulose ethers such as hydroxypropyl cellulose (HPC), and sugar alcohols such as xylitol, sorbitol or maltitol (2) proteins such as gelatin and (3) synthetic polymers including polyvinylpyrrolidone (PVP), polyethylene glycol (PEG). Binders are classified according to their application. Solution binders are dissolved in a solvent (for example water or alcohol can be used in wet granulation processes). Examples include gelatin, cellulose, cellulose derivatives, polyvinylpyrrolidone, starch, sucrose and polyethylene glycol. Dry binders are added to the powder blend, either after a wet granulation step, or as part of a direct powder compression (DC) formula. Examples include cellulose, methyl cellulose, polyvinylpyrrolidone and polyethylene glycol.

The terms "including", "such as", "for example" and the like are intended to refer to exemplary embodiments and not to limit the scope of the present disclosure.

Platinum(II) Complexes and Pharmaceutical Compositions Thereof

The present disclosure provides platinum(II) complexes having medicinal or pharmaceutical properties, preferably antitumor, anticancer and/or antiproliferative properties. In these platinum(II) complexes, each central platinum(II) atom is coordinated by four ligands, two of which are phosphine ligands or derivatives thereof and the other two ligands are each a heterocyclic thione, or a derivative or a tautomer thereof. Each heterocyclic thione ligand has a saturated five-, six- or seven-membered heterocyclic ring with two nitrogen atoms at positions 1 and 3 of the ring and a thiocarbonyl functional group at position 2. Specifically, each ligand is thione-based with an imidazolidine, tetrahydropyrimidine or 1,3-diazepane ring and their base, unsubstituted structures are shown as Formulas A-C below:

Formula A imidazolidine-2-thione

Formula B tetrahydropyrimidine-2(1H)-thione

Formula C 1,3-diazepane-2-thione

Each heterocyclic thione or phosphine ligand binds to the central platinum(II) atom in a monodentate manner. The sulfur atoms of the thiocarbonyl group and the phosphorus atoms of the phosphine groups act as electron donor atoms to which the platinum(II) atom is coordinated. In other words, the platinum(II) atom is coordinated to two donor sulfur atoms from two heterocyclic thione ligands and two donor phosphorus atoms from two phosphine ligands. Accordingly, a platinum(II) complex described herein has a generic structure of Formula I, Formula II, Formula III, Formula IV, Formula V or Formula VI:

Formula V

Formula VI or a pharmaceutically acceptable salt, tautomer, ester, solvate or prodrug thereof. $R_1$-$R_{18}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group.

Preferably, a Pt(II) complex of the present disclosure is in a cis-configuration and is therefore represented by Formula I, Formula III or Formula V, or a pharmaceutically acceptable salt, tautomer, ester, solvate or prodrug thereof, where $R_1$-$R_{18}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group.

Preferably, $R_1$-$R_{18}$ are each independently a hydrogen, a halogen, an optionally substituted $C_1$-$C_2$ alkyl group, an optionally substituted $C_1$-$C_2$ alkoxy group, an optionally substituted $C_2$ alkenyl group or an optionally substituted $C_2$ alkynyl group.

More preferably, $R_1$-$R_6$ are each an ethyl group, $R_7$-$R_{10}$ are each a hydrogen, a methyl group or an ethyl group, and $R_{11}$-$R_{18}$ are each a hydrogen.

Even more preferably, the Pt(II) complex is one of the following:

cis-bis(triethylphosphine)di(imidazolidine-2-thione)platinum(II);
cis-bis(triethylphosphine)di(1-methylimidazolidine-2-thione)platinum(II);
cis-bis(triethylphosphine)di(1,3-dimethylimidazolidine-2-thione)platinum(II);
cis-bis(triethylphosphine)di(1,3-diethylimidazolidine-2-thione)platinum(II);
cis-bis(triethylphosphine)di(imidazolidine-2-thione)platinum(II);
cis-bis(triethylphosphine)di(tetrahydropyrimidine-2(1H)-thione)platinum(II);
cis-bis(triethylphosphine)di(1-methyltetrahydropyrimidine-2(1H)-thione)platinum(II); and
cis-bis(triethylphosphine)di(1,3-diazepane-thione)platinum(II).

In certain embodiments, especially but not limited to pharmaceutical applications, the platinum(II) complex can further include a counter-anion to form a pharmaceutically acceptable salt. As used herein, the term "counter-anion" refers to an anion, preferably a pharmaceutically acceptable anion that is associated with a positively charged platinum (II) complex of at least one of the Formulas 1-3. Non-limiting examples of pharmaceutically counter-anions include halides such as fluoride, chloride, bromide, iodide; nitrate; sulfate; phosphate; amide; methanesulfonate; ethanesulfonate; p-toluenesulfonate, salicylate, malate, maleate, succinate, tartarate; citrate; acetate; perchlorate; trifluoromethanesulfonate (triflate); acetylacetonate; hexafluorophosphate; and hexafluoroacetylacetonate. In some embodiments, the counter-anion is a halide, preferably chloride.

Another aspect of the present disclosure relates to pharmaceutical composition comprising one or more of the platinum(II) complexes described herein. In other words, the platinum(II) complexes described herein or analogues or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of one or more of the platinum(II) complexes described herein or derivatives thereof in combination with a pharmaceutically acceptable carrier and, in addition, may include other medicinal agents, pharmaceutical agents, carriers, diluents or other non-active ingredients. By pharmaceutically acceptable is meant a material that is not biologically or otherwise undesirable, which can be administered to an individual along with the selected compound without causing significant unacceptable biological effects or interacting in a deleterious manner with the other components of the pharmaceutical composition in which it is contained.

A platinum(II) complex of the present disclosure or an analogue or derivative thereof may be used in conjunction with one or more additional compounds, in the treatment or prevention of neoplasm; of tumor or cancer cell division, growth, proliferation and/or metastasis in a mammalian subject; induction of death or apoptosis of tumor and/or cancer cells; and/or any other form of proliferative disorder. A platinum(II) complex of the present disclosure can be formulated as a pharmaceutical composition.

The neoplastic activity of the tumor or cancer cells may be localized or initiated in one or more of the following: blood, brain, bladder, lung, cervix, ovary, colon, rectum, pancreas, skin, prostate gland, stomach, breast, liver, spleen, kidney, head, neck, testicle, bone (including bone marrow), thyroid gland, central nervous system. The platinum(II) complex of the present disclosure or the pharmaceutical composition thereof is especially effective in the treatment or prevention of colorectal cancer (including colon cancer, rectum cancer and bowel cancer); lung cancer (including non-small cell lung carcinoma or NSCLC and small cell lung carcinoma); cervical cancer (including the histologic subtypes of squamous cell carcinoma, adenocarcinoma, adenosquamous carcinoma, small cell carcinoma, neuroendocrine tumor, glass cell carcinoma, villoglandular adenocarcinoma, melanoma and lymphoma).

A pharmaceutical composition comprising one or more platinum(II) complexes of the present disclosure can be administered orally, systemically, parenterally, by inhalation spray, rectally, or topically in dosage unit formulations containing conventional nontoxic pharmaceutically acceptable carriers, adjuvants, and vehicles as desired. In some embodiments, the method of administration of the steroid or an analogue or derivative thereof is oral. In other embodiments, the compound or an analogue or derivative thereof is administered by injection, such as, for example, through a peritumoral injection.

Topical administration can also involve the use of transdermal administration such as transdermal patches or iontophoresis devices. The term parenteral as used herein includes intravesical, intradermal, transdermal, subcutaneous, intramuscular, intralesional, intracranial, intrapulmonal, intracardial, intrastemal and sublingual injections, or infusion techniques. Formulation of drugs is discussed in, for example, Hoover, John E., Remington's Pharmaceutical Sciences, Mack Publishing Co., Easton, Pa.; 1975. Another example of includes Liberman, H. A. and Lachman, L., Eds., Pharmaceutical Dosage Forms, Marcel Decker, New York, N.Y., 1980, which is incorporated herein by reference in its entirety.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful. Suppositories for rectal administration of the compound or an analogue or derivative thereof can be prepared by mixing the steroid or an analogue or derivative thereof with a suitable nonirritating excipient such as cocoa butter, synthetic mono- di- or triglycerides, fatty acids and polyethylene glycols that are solid at ordinary temperatures but liquid at the rectal temperature and will therefore melt in the rectum and release the drug.

Solid dosage forms for oral administration can include capsules, tablets, pills, powders, and granules. In such solid dosage forms, the compounds of this disclosure are ordinarily combined with one or more adjuvants appropriate to the indicated route of administration. If administered per os, a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated steroid or an analogue or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredients that can be combined with the carrier materials to produce a single dosage form varies depending upon the mammalian subject treated and the particular mode of administration.

Methods of Synthesizing Platinum(II) Complexes

The platinum(II) complexes of the present disclosure are not limited by their synthesis routes and methods. These platinum(II) complexes can be prepared by various previously reported synthesis protocols with appropriate modification [A. Z. A. Mustafa, M. Altaf, M. Monim-ul-Mehboob, M. Fettouhi, M. I. M. Wazeer, A. A. Isab, V. Dhuna, G. Bhatia, K. Dhuna, Inorg. Chem. Commun., 44 (2014) 159; G. D. Thorn, Can. J. Chem. 33 (1955) 1278-1280; L. Maier, Helv. Chim. Acta, 53 (1970) 1417—each incorporated herein by reference in its entirety].

In one embodiment, the heterocyclic thione ligands coordinating the central core platinum(II) atom are prepared by reacting carbon disulfide ($CS_2$) with diamines in diethyl ether solvent and refluxing the reaction mixture at 100-110° C. for 2-3 h. The clear yellow product was recrystallized from methanol.

In one embodiment, to prepare a Pt(II) complex having chloride as the counter anion, 2-3 equivalents of a heterocyclic thione solution (e.g. 1.0-5.0 mmol, dissolved in 10-20 ml of methanol) are added drop wise to a (diphosphine) platinum(II)chloride solution (e.g. 0.5-2.5 mmol, dissolved ml 0-20 ml of dichloromethane). The resulting mixture is stirred for 2-5 h to produce a colored solution, then filtered and kept at room temperature until a solid powder is obtained on slow evaporation of all solvents from the complexes.

Method of Inhibiting Proliferation of Cancer Cells and Inducing Cancer Cell Death The present disclosure further provides a method of inhibiting proliferation of human cancer cells and inducing apoptosis of the human cancer cells in vitro or in vivo. Human cancer cells are contacted with 1-100 µM of a gold(III) complex in accordance with the present disclosure or a composition comprising the gold(III) complex at the defined concentration range, preferably 2-80 µM, more preferably 5-75 µM, even more preferably 10-60 µM, 12.5-60 µM, 15-60 µM, 20-60 µM, most preferably 20-55 µM, 25-55 µM 30-55 µM, 35-55 µM, 30-40 µM, 25-40 µM, 35-45 µM, 40-50 µM, 45-50 µM. The viability of cells can be determined by standard cell viability assays such as but not limited to ATP test, Calcein AM assay, clonogenic assay, ethidium homodimer assay, Evans blue assay, Fluorescein diacetate hydrolysis/propidium iodide staining assay, flow cytometry assay, formazan-based assays (MTT.XTT), green fluorescent protein assay, lactate dehydrogenase assay, methyl vilet assay, propidium iodide assay, Resazurin assay, Trypan Blue assay and TUNEL assay.

When contacted with one or more of the platinum(II) complexes at the defined concentration, the viability of the human cancer cells is reduced to at least 95%, preferably at least 85%, more preferably at least 75%, even more preferably at least 50%, at least 45%, at least 40%, at least 35%, at least 30%, at least 25%, at least 20%, most preferably at least 15%, at least 12.5%, at least 10%, at least 7.5%, at least 5%, at least 2.5%, at least 2%, at least 1% and at least 0.5%.

The half maximal inhibitory concentration ($IC_{50}$) is a measure of the effectiveness of a substance in inhibiting a specific biological or biochemical function. The $IC_{50}$ values of the gold(III) complexes against the human cancer cells are no higher than 50 µM, preferably no higher than 40 µM, more preferably no higher than 30 µM, no higher than 25 µM, even more preferably no higher than 20 µM, no higher than 15 µM, most preferably no higher than 12.5 µM, no higher than 10 µM and no higher than 5 µM. In some embodiments, the $IC_{50}$ value of the platinum complexes against human cervical, lung, breast or colon cancer cells, such as but not limited to HeLa, A549, MCF-7 and HCT15 human cancer cell lines, are ranged 0.1-50 µM, preferably 0.5-40.0 µM, more preferably 1.0-20.0 µM, even more preferably 1.0-10.0 µM, most preferably 1.0-9.0 µM, 1.0-8.5 µM, 1.0-8.0 µM, 1.0-7.5 µM, 1.0-7.0 µM, 1.0-6.5 µM, 1.0-6.0 µM, 1.0-5.5 µM, 1.0-5.0 µM, 1.0-4.5 µM, 1.0-4.0 µM, 1.0-3.5 µM, 1.0-3.0 µM, 1.0-2.5 µM, 1.0-2.0 µM, 1.0-1.5 µM. In some embodiments, compared to cisplatin and carboplatin, the $IC_{50}$ values of the platinum(II) complexes provided herein are up to 50% lower, preferably 5-50% lower, more preferably 10-50% lower, even more preferably 25-50% times lower.

In some embodiments, the human cancer cells are derived from commercial cell line models, including but are not limited to HeLa cervical cancer cells, A549 lung cancer cells, HCT-15 colon cancer cells, HCT-8 or HRT-8 colon cancer cells, DLD-1 colon cancer cells, MCF-7 breast cancer cells, A2780 ovarian cancer cells, A2780-cis cisplatin-resistant ovarian cancer cells, PC3 prostatic cancer cells, DU-145 prostatic cancer cells, SGC7901 gastrointestinal cancer cells and SGC7901—cis cisplatin-resistant gastrointestinal cancer cells.

In other embodiments, the human cancer cells are cancer cells of a human patient who has been diagnosed with, is suspected of having, or is susceptible to or at risk of having at least one form of cancer, preferably prostate cancer and/or gastrointestinal cancer.

Methods of Treating Cancers and Combination Therapies

Cancers such as but not limited to sarcomas, carcinomas, melanomas, myelomas, gliomas and lymphomas can be treated or prevented with the platinum(II) complexes provided herein. In some embodiments, methods incorporating the use of at least one of the platinum(II) complexes of the present disclosure are effective in the treatment or prevention of cancer of the blood, brain, bladder, lung, cervix, ovary, colon, rectum, pancreas, skin, prostate gland, stomach, breast, liver, spleen, kidney, head, neck, testicle, bone (including bone marrow), thyroid gland or central nervous system. In some embodiments, these methods are especially effective in the treatment or prevention of cervical, colon and lung cancers.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, after treatment with one or more platinum(II) complexes or a pharmaceutical composition thereof, the size of a tumor, whether by volume, weight or diameter, is reduced by at least 5%, 10%, 15%, 20%, 25%, 30%, 40%, 50%, 60%, 70%, 75%, 80%, 85%, 90%, 95%, 99% or 100%, relative to the tumor size before treatment. In other embodiments, after treatment with the one or more platinum(H) complexes of a pharmaceutical composition thereof, the size of a tumor does not reduce but is maintained the same as the tumor size before treatment. Methods of assessing tumor size include but are not limited to CT Scan, MRI, DCE-MRI and PET Scan.

In some embodiments, the method for treating cancer and other proliferative disorders involves the administration of a unit dosage or a therapeutically effective amount of one or more of platinum(II) complexes or a pharmaceutical composition thereof to a mammalian subject (preferably a human subject) in need thereof. As used herein, "a subject in need thereof" refers to a mammalian subject, preferably a human subject, who has been diagnosed with, is suspected of having, is susceptible to, is genetically predisposed to or is at risk of having at least one form of cancer. Routes or modes of administration are as set forth herein. The dosage and treatment duration are dependent on factors such as bioavailability of a drug, administration mode, toxicity of a drug, gender, age, lifestyle, body weight, the use of other drugs and dietary supplements, cancer stage, tolerance and resistance of the body to the administered drug, etc., then determined and adjusted accordingly. The one or more of platinum(II) complexes or a pharmaceutical composition thereof may be administered in a single dose or multiple individual divided doses. In some embodiments, the interval of time between the administration of platinum(II) complexes or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, mixed diamine ligand platinum(II) complexes and one or more additional therapies are administered less than 1 day, 1 week, 2 weeks, 3 weeks, 4 weeks, one month, 2 months, 3 months, 6 months, 1 year, 2 years, or 5 years apart.

A physician or veterinarian having ordinary skill in the art can readily determine and prescribe the therapeutically effective amount of the pharmaceutical composition required. For example, the physician or veterinarian could start doses of the platinum(II) complexes of the invention employed in the pharmaceutical composition at levels lower than that required in order to achieve the desired therapeutic effect and gradually increase the dosage until the desired effect is achieved.

In general, a suitable daily dose of a platinum(II) complex of the present disclosure will be that amount of the compound which is the lowest dose effective to produce a therapeutic effect. Such an effective dose will generally depend upon the factors described above. Generally, oral, intravenous, intracerebroventricular and subcutaneous doses of the platinum(II) complex of this invention for a patient will range from 0.01-100 mg per kilogram of body weight per day (24 h), preferably 0.05-75 mg/kg/day, more preferably 0.1-50 mg/kg/day, even more preferably 0.5-50 mg/kg/day, 1.0-50 mg/kg/day, 5.0-50 mg/kg/day, 10-50 mg/kg/day, 20-50 mg/kg/day, 25-50 mg/kg/day.

If desired, the effective daily dose of the active compound, which is the platinum(II) complex in the present case, may be administered as two, three, four, five, six or more sub-doses administered separately at appropriate intervals throughout the day, optionally, in unit dosage forms. In certain aspects of the invention, dosing is one administration per day.

While it is possible for a platinum(II) complex of the present disclosure to be administered alone, it is preferable to administer the platinum(II) complex as a pharmaceutical formulation (composition).

In certain embodiments, a platinum(II) complex of the present disclosure or a pharmaceutical composition thereof may be used in combination with one or more other active pharmaceutical agents, preferably antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cisplatin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Examples for antineoplastic agents which are antibodies comprise trastuzumab, cetuximab, panitumumab, rituximab, bevacizumab, mapatumumab, conatumumab, lexatumumab and the like. In one embodiment, a pharmaceutical composition may be formulated as such to incorporate at least one platinum(II) complex of the present disclosure and one or more other active pharmaceutical agents which may or may not be selected from the list above.

EXAMPLES

The following examples have been included to further describe protocols for synthesizing and characterizing certain Pt(II) complexes having mixed phosphine-based and heterocyclic thione ligands, and results thereof. It should be noted that these examples have been included for illustrative purposes, and are not intended to limit the scope of the appended claims.

The following examples describe the synthesis and characterization of seven new Pt(II) complexes with general formula cis-$[(Et_3P)_2Pt(L)_2]Cl_2$, (L=Thione), as alternatives to conventional platinum-based drugs, especially cisplatin and carboplatin since these two drugs are associated with severe side toxic effects. The synthesized complexes were characterized using different techniques such as elemental analysis, FTIR and $^1H$, $^{13}C$ NMR measurements. The complexes were tested in vitro cytotoxicity against four cell lines: HeLa (human squamous cervical adenocarcinoma), MCF-7 (human breast carcinoma), A549 (human lung carcinoma), and HCT15 (human colon carcinoma). The $IC_{50}$ values of new complexes range from 1.40±0.29 to 17.27±1.34, 2.37±0.29 to 27.73±1.48, 1.23±0.34 to 22.33±1.35 and 4.23±0.73 to 37.10±1.86 μM for HeLa, A549, MCF-7 and HCT15 cancer cell lines respectively. Complexes (1)-(6) showed rapid interaction with human cancer cell lines and were found to be more efficient than cisplatin and carboplatin against HeLa (human cervical cancer), A549 (human lung cancer), MCF-7 (human breast cancer) and HTC15 (human colon cancer) cell lines. The in vitro cell viability and $IC_{50}$ values of complexes (1)-(6) are much better than those of cisplatin and carboplatin, thereby supporting the hypothesis that changing the coordination atmosphere around a Pt(II) ion in new compounds can significantly enhance the anticancer efficacy of the complex.

Example 1

Materials and Methods cis-Bis(triethylphosphine)platinum(II)chloride, $[(Et_3P)_2PtCl_2]$ was purchased from Strem Chemicals, Inc. Carbon disulfide ($CS_2$). Diamines, i.e. N-methyl-1,2-diaminoethane, N-ethyl-1,2-diaminoethane, N-propyl-1,2-diaminoethane and N-isopropyl-1,2-diaminoethane, N-ethyl-1,3-Diaminopropane, 1,4-Diaminobutane, were obtained from Sigma Aldrich. Dulbecco's Modified Eagle Medium (DMEM), (3-(4,5-Dimethylthiazol-2-yl)-2,5-Diphenyltetrazolium Bromide) (MTT), Dimethyl sulfoxide (DMSO) and deuterated solvents were also obtained from Sigma Aldrich Chemical Co. All other solvents were obtained from Fluka Chemical Co. and used without further purification.

The heterocyclic thione ligands were synthesized following a literature procedure by the reaction of carbon disulfide ($CS_2$) with diamines in diethyl ether solvent. The mixture was then refluxed at 100-110° C. for 2-3 h. The clear yellow product was recrystallized from methanol [G. D. Thorn, Can. J. Chem. 33 (1955) 1278-1280; L. Maier, Helv. Chim. Acta, 53 (1970) 1417—each incorporated herein by reference in its entirety].

Elemental analyses were performed on Perkin Elmer Series 11 (CHNS/O), Analyzer 2400. The solid state FTIR spectra of the ligands and their Platinum(II) complexes were recorded on a Perkin-Elmer FTIR 180 spectrophotometer or NICOLET 6700 FTIR using KBr pellets over the range 4000-400 $cm^{-1}$.

$^1H$, and $^{13}C$ NMR spectra were recorded on a LAMBDA 500 spectrophotometer operating at 500.01, 125.65 and 200.0 MHz respectively, corresponding to a magnetic field of 11.74 T. Tetramethylsilane (TMS) was used as an internal standard for $^1H$ and $^{13}C$. The $^{13}C$ NMR spectra were obtained with $^1H$ broadband decoupling, and the spectral conditions were: 32 k data points, 0.967 s acquisition time, 1.00 s pulse delay and 45° pulse angle [Z. Popovic, G. Pavlovic, D. Matkovic-Calogovic, Z. Soldin, M. Rajic, D.

Vikic-Topic, D. Kovacek, Inorg. Chim Acta, 306 (2000) 142-152—incorporated herein by reference in its entirety].

Example 2

Synthesis of Pt(II) Complexes

Each of the synthesized Pt(II) complexes (1)-(7) has two bis(triethylphosphine) ligands and two heterocyclic thione ligands that are represented by the structures in Table 1.

TABLE 1

Skeletal structures of different heterocyclic thione ligands of Pt complexes (1)-(7).

| Complex | Description of heterocyclic thione ligands and R groups |
|---|---|
| 1 | R = R/ = H; Imidazolidine-2-thione (Imt). |
| 2 | R = $CH_3$, R/ = H; N-methylimidazolidine-2-thione (MeImt). |
| 3 | R = R/ = $CH_3$; N, N/-dimethylimidazolidine-2-thione ($Me_2$Imt). |
| 4 | R = R/ = $C_2H_5$; N, N/-diethylimidazolidine-2-thione ($Et_2$Imt). |
| 5 | R = H; 1,3-Diazinane-2-thione (Diaz). |
| 6 | R = $C_2H_5$; N-ethyl-1,3-diazinane-2-thione (EtDiaz). |
| 7 | 1,3-Diazipane-2-thione (Diap). |

To prepare a Pt(II) complex, two equivalents of thione solution (1.0 mmol, dissolved in 10 ml methanol) was added drop wise to (250 mg, 0.5 mmol, dissolved in 10 ml dichloromethane) of $[(Et_3P)_2PtCl_2]$ solution. The resulting mixture was stirred for 3 h which resulted in a colored solution. After the reaction solution was filtered and kept at room temperature, solid powder was obtained on slow evaporation of the solvent for all complexes. Melting points, elemental analysis (CHNS) %, NMR chemical shifts and IR spectroscopic characterization results are tabulated in Tables 2, 3 and 4 respectively.

where L=Imt; complex (1), MeImt; complex (2), $Me_2$Imt; complex (3), $Et_2$Imt; complex (4), Diaz; complex (5), EtDiaz; complex (6), Diap; complex (7).

TABLE 2

Melting point and elemental analysis data for the synthesized Pt(II) complexes.

| Complex | Chemical composition calculated and found (%) | | | | M.p. (° C.) | Color | Yield (%) |
|---|---|---|---|---|---|---|---|
| | C | H | N | S | | | |
| (1) | 30.59 (30.49) | 6.00 (7.22) | 7.93 (8.03) | 9.07 (8.61) | 223-225 | White | 89 |
| (2) | 32.69 (33.04) | 6.32 (6.18) | 7.63 (8.11) | 8.73 (8.11) | 246-250 | White | 82 |
| (3) | 34.64 (35.84) | 6.62 (5.88) | 7.35 (8.46) | 8.40 (8.46) | 214-216 | Yellow | 69 |
| (4) | 38.13 (36.99) | 7.15 (7.36) | 6.84 (6.92) | 7.83 (8.08) | 189-191 | Yellow | 73 |
| (5) | 32.56 (34.04) | 6.30 (8.96) | 7.60 (7.63) | 8.69 (8.46) | 208-210 | Brown | 84 |
| (6) | 36.45 (36.01) | 6.90 (6.66) | 7.09 (5.89) | 8.11 (9.41) | 188-190 | White | 67 |
| (7) | 34.64 (36.22) | 6.62 (7.96) | 7.35 (7.63) | 8.41 (8.46) | 159-161 | Yellow | 77 |

Example 3

In Vitro Cytotoxic Activity Against HeLa, A549, MCF7 and HCT15 Human Cancer Cell Lines A Pt(II) metal precursor, cisplatin, carboplatin and seven synthesized complexes (1)-(7) were evaluated for their in-vitro cytotoxic activity against HeLa (human cervical cancer), A549 (human lung cancer), MCF-7 (human breast cancer) and HTC15 (human colon cancer) cell lines.

The cells were seeded at $4 \times 10^3$ cells/well in 100 μL DMEM (Dulbecco's Modified Eagle's Medium) containing 10%. FBS (Fetal Bovine Serum) in 96-well tissue culture plate and incubated for 72 h at 37° C., 5% $CO_2$ in air and 90% relative humidity in $CO_2$ incubator. After incubation, 100 μL of new complexes (1)-(7), Pt(II) precursor, cisplatin and carboplatin (50, 25, 12.5 and 6.25 μM), prepared in DMEM, was added to cells and the cultures were incubated for 24 h. The medium of wells was discarded and 100 μL DMEM containing MTT (3-(4,5-dimethylthiazol-2-Yl)-2,5-diphenyltetrazolium bromide) (5 mg/mL) was added to the wells and incubated in $CO_2$ incubator at 37° C. in dark for 4 h. After incubation, a purple colored formazan (artificial chromogenic dye, product of the reduction of water insoluble tetrazolium salts e.g., MMT by dehydrogenases and reductases) in the cells is produced and appeared as dark crystals in the bottom of the wells. The medium of culture was discarded from each well carefully to avoid disruption of monolayer and 100 μL of dimethylsufoxide (DMSO) was added in each well. The solution was thoroughly mixed in the wells to dissolve the formazan crystals which ultimately result into a purple solution. The absorbance of the 96-wells plate was taken at 570 nm with Labsystems Multiskan EX-Enzyme-linked immunosorbent assay (EX-ELISA) reader against a reagent blank. The $IC_{50}$ values were calculated from three independent experiments by generating an equation of logarithmic trendline of percentage cell viability against concentration of compounds in Microsoft Excel.

Example 4

Nuclear Magnetic Resonance (NMR) Spectroscopic Characterization

All the signals of the free thione ligand molecules detected in the $^1H$ and $^{13}C$ NMR spectra of the appropriate starting compounds (ligands) were also found in the spectra of the Pt(II) complexes. The N—H signal of thiones become less intense upon coordination and shifted slightly toward high frequency from 0.8-1.4 with respect to their positions in free ligands However, these signals were shifted as a consequence of the coordination of ligands to the Pt(II) atom and the formation of the targeting products. The deshielding of the N—H proton is related to an increase of the π electron density in the C—N bond upon complexation, which indicates that the ligands were coordinated to the platinum center through the sulfur atom not via nitrogen [Seerat-ur-Rehman, A. A. Isab, M. N. Tahir, T. Khalid, M. Saleem, H. Sadaf, S. Ahmad, Polyhedron, 36 (2013) 68-71—incorporated herein by reference in its entirety].

$^{13}$C NMR chemical shifts of the free ligands and their complexes are given in Table 3, In all of the Pt(II) complexes, C-2 signals correspond to C=S resonance and appears in the lower frequency by 6-9 ppm compared to free ligands. This shifts is attributed to decrease in the bond order of C=S bond upon coordination and shift of electron density from N→C producing a partial double bond character in the C—N bond [.N. O. K. A. Al-Sadhan, A. A. Isab, M. I. M. Wazeer, and A. R. A. Al-Arfaj, Spectroscopy, 21(2007) 61-67—incorporated herein by reference in its entirety]. The thiocarbonyl carbon resonance shift is attributed to coordination of thion ligand through sulfur atom to Pt(II) ion, as observed in the other platinum (II) complexes of thione ligands [S. A. Tirmizi, S. Nadeem, A. Hameed, M. H. S. Wattoo, A. Anwar, Z. A. Ansari, S. Ahmad, Spectroscopy, 23 (2009) 299-306—incorporated herein by reference in its entirety].

TABLE 3

$^1$H and $^{13}$C NMR chemical shifts of the free ligands and their complexes in CDCl$_3$.

| Species (Complex) | N—H | C-2 | C-4 | C-5 | C-6 | C-7 | N-C1 | N-C2 |
|---|---|---|---|---|---|---|---|---|
| Imt | 7.98 | 182.11 | 45.38 | 45.38 | — | — | — | — |
| (1) | 9.19 | 174.50 | 46.60 | 46.60 | — | — | — | — |
| MeImt | 7.93 | 181.38 | 42.00 | 51.82 | — | — | 34.35 | — |
| (2) | 8.65 | 174.32 | 42.56 | 52.13 | — | — | 34.47 | — |
| Me$_2$Imt | — | 180.46 | 48.73 | 48.73 | — | — | 34.80 | — |
| (3) | — | 174.33 | 49.71 | 49.71 | — | — | 35.16 | — |
| Et$_2$Imt | — | 178.74 | 46.13 | 46.13 | — | — | 42.69 | 11.92 |
| (4) | — | 171.94 | 47.38 | 47.38 | — | — | 43.77 | 12.08 |
| Diaz | 7.77 | 173.34 | 38.36 | 19.29 | 38.36 | 19.29 | — | — |
| (5) | 9.13 | 166.68 | 41.53 | 19.92 | 41.53 | 19.92 | — | — |
| Et-Diaz | 7.70 | 173.36 | 41.14 | 20.93 | 46.14 | — | 49.54 | 12.33 |
| (6) | 8.32 | 168.24 | 41.35 | 20.91 | 47.03 | — | 49.66 | 12.43 |
| Diap | 7.70 | 183.99 | 45.86 | 26.70 | 45.86 | 26.70 | — | — |
| (7) | 8.50 | 175.22 | 46.44 | 26.46 | 46.44 | 26.46 | — | — |

Example 5

Fourier Transform Infrared (FT-IR) Spectroscopic Characterization

Selected infra-red spectroscopic vibrational bands for the free ligands and their platinum (II) complexes are given in Table 4. In the IR spectrum of thiones, the characteristic bands are observed in two frequency regions; thiocarbonyl ν(C=S) appears around 600 cm$^{-1}$ for the free ligands, This shifts towards lower frequency upon complexation, in accordance with the data showed for the other thione complexes, another important vibrational band of ν(N—H) was noticed near 3200 cm$^{-1}$ Upon coordination to Pt(II) this band shifts to higher wave numbers. The presence of (C=S) as well as (N—H) vibration bands in the complexes confirms that the thione forms of the ligands in the solid state [W. Ashraf, S. Ahmad, and A. A. Isab, Transit. Met. Chem., 29 (2004) 400-404; A. A. Isab, S. Ahmad and M. Arab, Polyhedron, 21 (2002) 1267-1271—each incorporated herein by reference in its entirety].

TABLE 4

FT-IR spectra assignments for free ligands absorption bands (cm$^{-1}$) and their complexes.

| Species | IR Frequency (cm$^{-1}$) | | |
|---|---|---|---|
| (Complex) | ν (C=S) | ν (N—H) | ν (M-S) |
| Imt | 1199 | 3200 | — |
| (1) | 1034 | 3446 | 272 |
| MeImt | 1200 | 3200 | — |
| (2) | 1052 | 3418 | 280 |
| Me$_2$Imt | 1201 | — | — |
| (3) | 1048 | — | 281 |
| Et$_2$Imt | 1199 | — | — |
| (4) | 1088 | — | 279 |
| Diaz | 1217 | 3210 | — |
| (5) | 1043 | 3422 | 282 |
| Et-Diaz | 1206 | 3210 | — |
| (6) | 1038 | 3448 | 274 |
| Diap | 1190 | 3214 | — |
| (7) | 1034 | 3521 | 267 |

Example 6

In Vitro Cytotoxic Effects of Pt(II) Complexes (1)-(7)

Preliminary anti-cancer activity studies were carried out on seven synthesized Pt(II) complexes (1)-(7), Pt(II) precursor, cisplatin and carboplatin against four cancer cell lines HeLa, A549, HCT15 and MCF-7 (human cancer cell lines) and an MTT assay was used to determine their dose-dependent cytotoxicity after 72 h [U. Bierbach, T. W. Hambly, N. Farrell, Inorg. Chem. 37 (1998) 708; L. Giovagnini, L. Ronconi, D. Aldinucci, D. Lorenzon, S. Sitran, and D. Fregona, J. Med. Chem. 48 (2005) 1588-1595—each incorporated herein by reference in its entirety].

Figure 1:
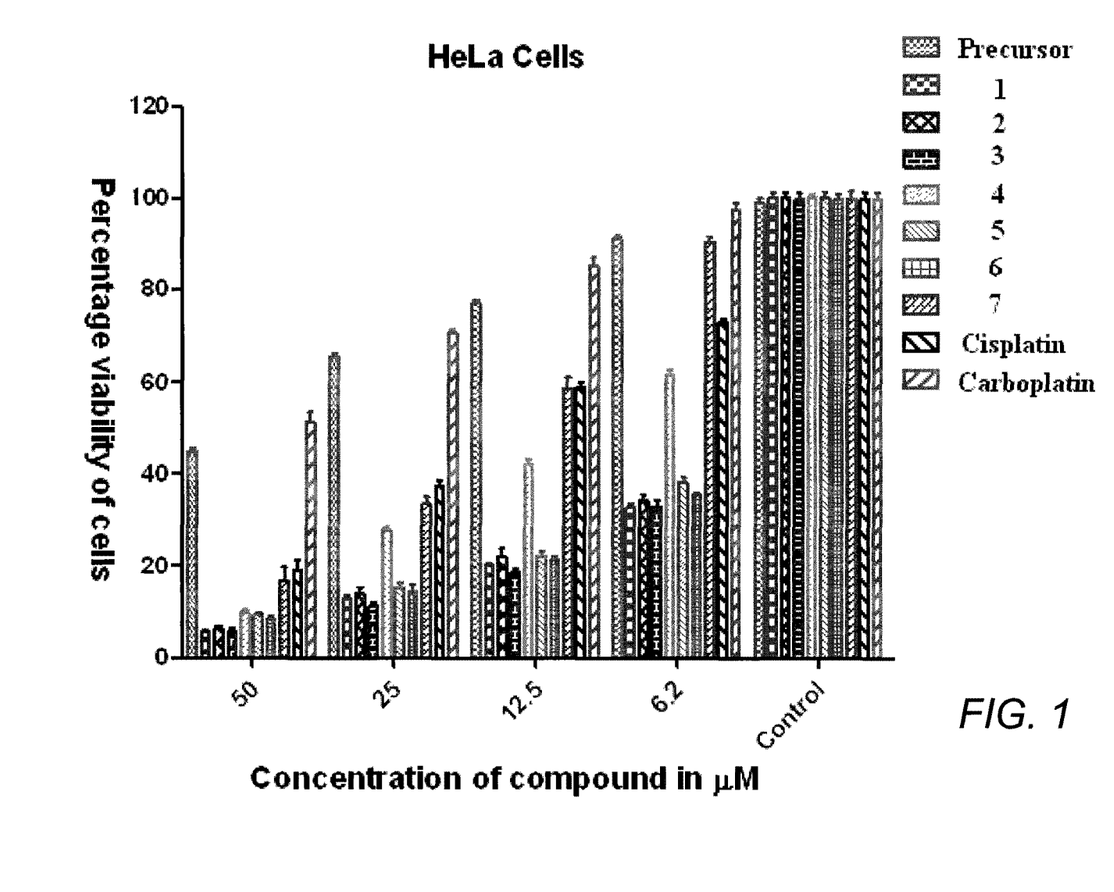
FIG. 1 is a graph showing the concentration dependent in vitro cytotoxic effect of complexes (1)-(7), precursor, cisplatin and carboplatin on viability of HeLa cancer cells.
Figure 2:
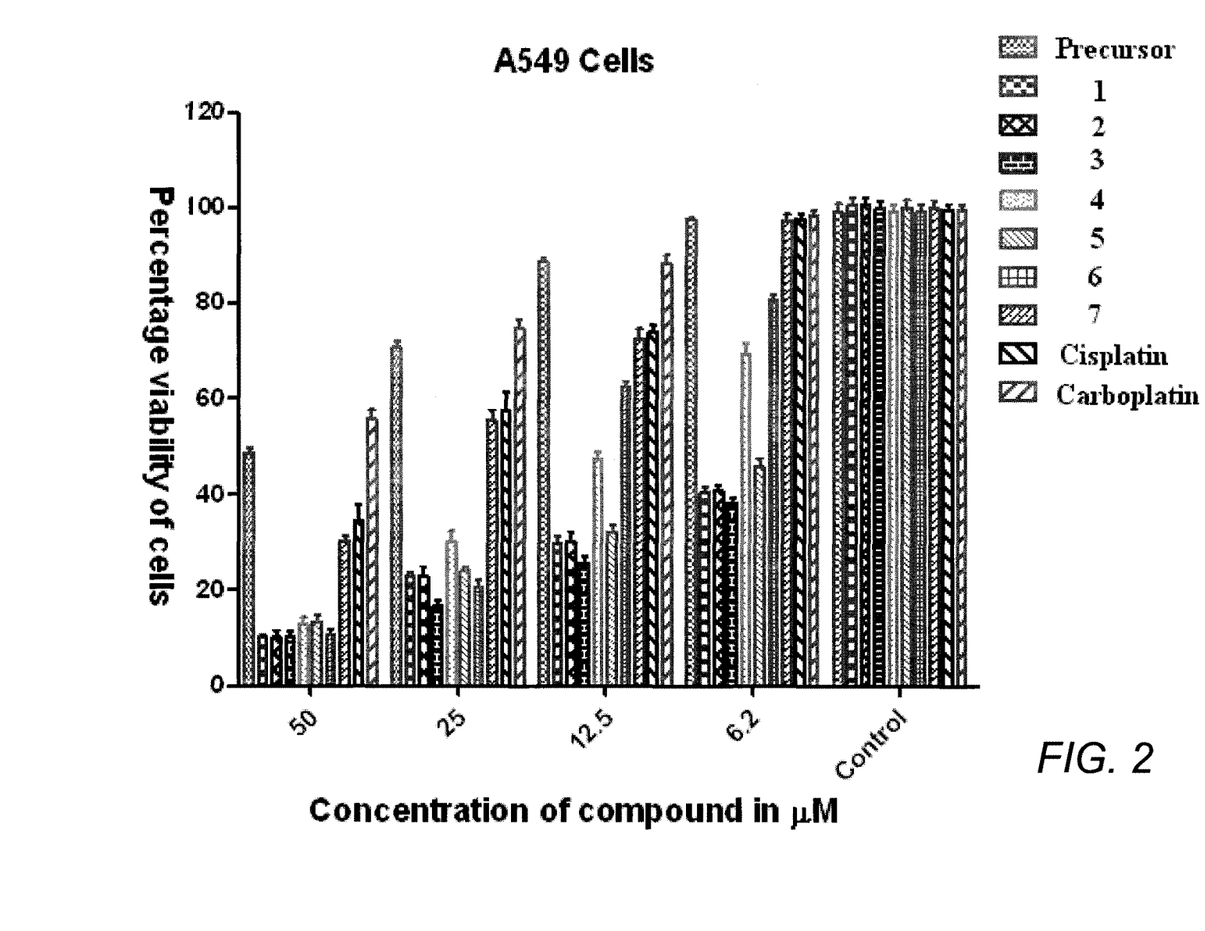
FIG. 2 is a graph showing the concentration dependent in vitro cytotoxic effect of complexes (1)-(7), precursor, cisplatin and carboplatin on viability of A549 cancer cells.
Figure 3:
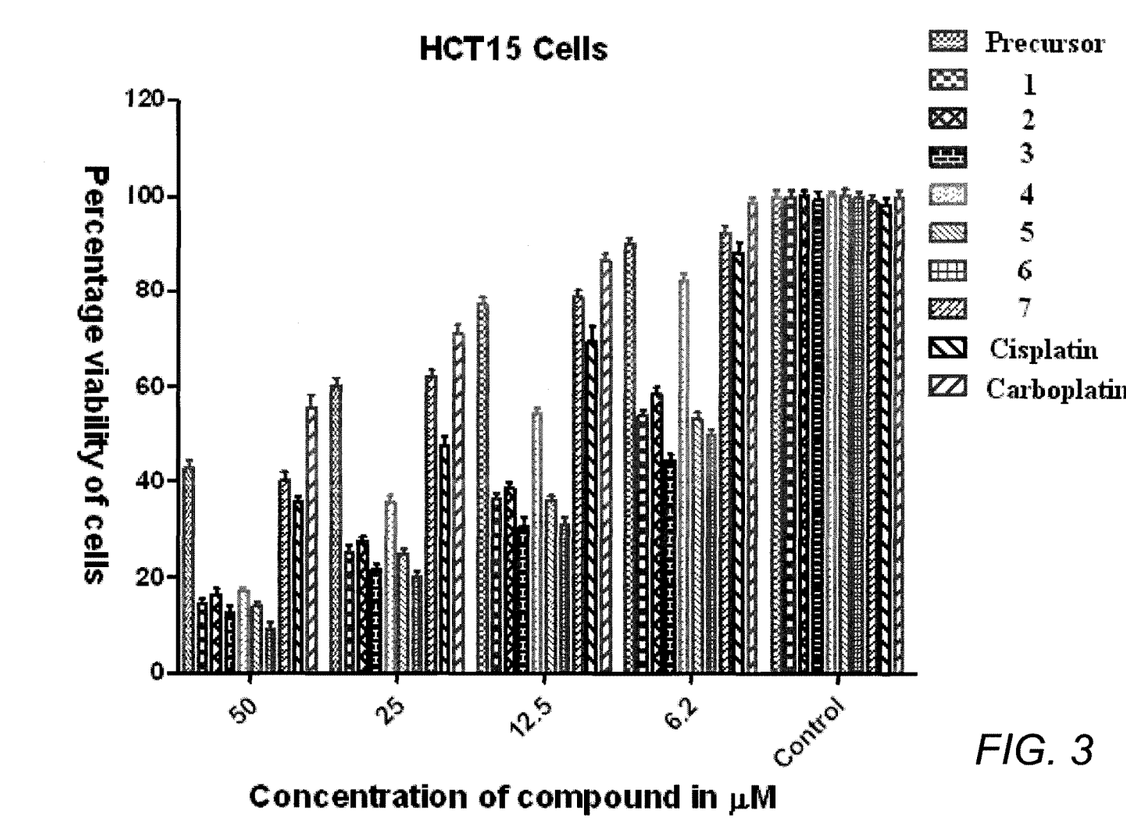
FIG. 3 is a graph showing the concentration dependent in vitro cytotoxic effect of complexes (1)-(7), precursor, cisplatin and carboplatin on viability of HCT15 cancer cells.
Figure 4:
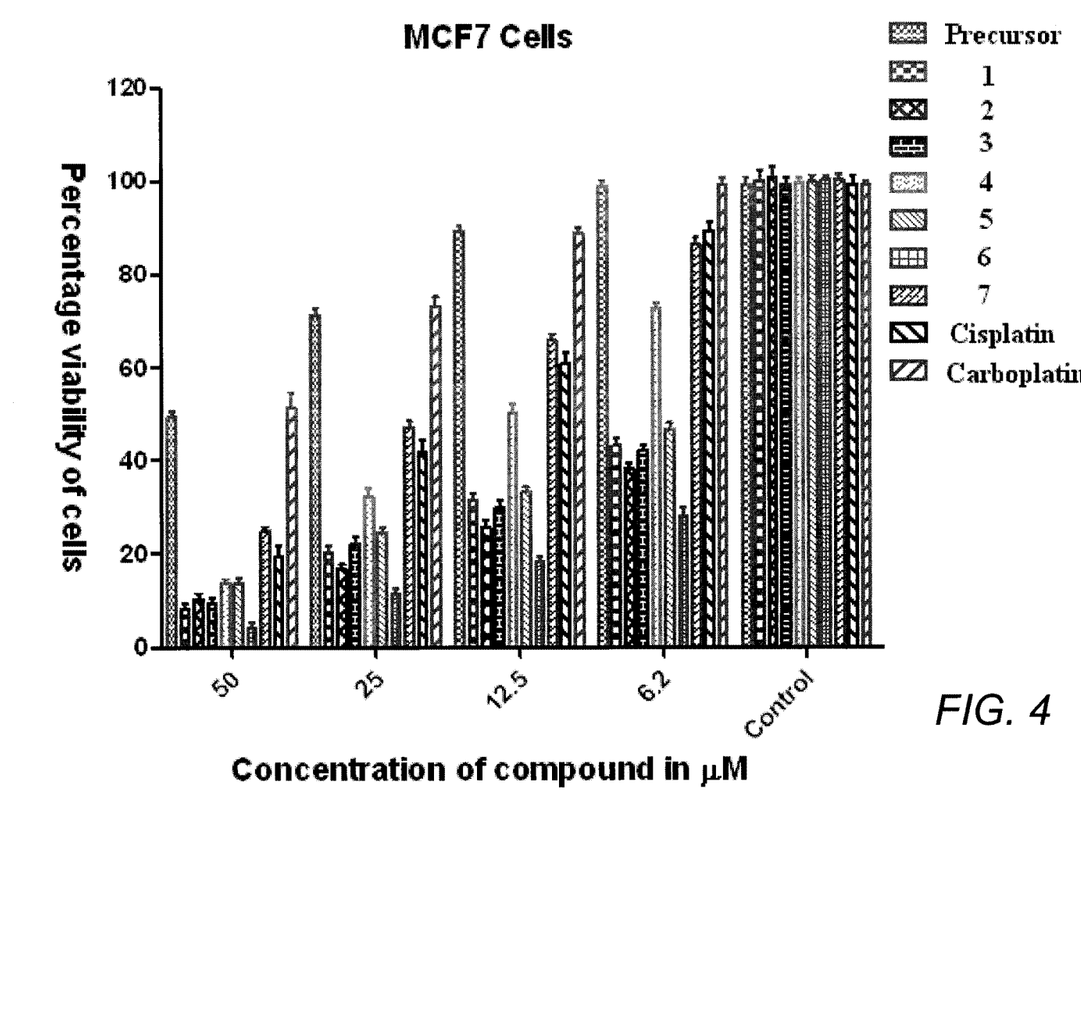
FIG. 4 is a graph showing the concentration dependent in vitro cytotoxic effect of complexes (1)-(7), precursor, cisplatin and carboplatin on viability of MCF7 cancer cells.

The in vitro MTT assay results show that six new complexes (1)-(6) have higher activity than the two standard anticancer drugs available in market (i.e. cisplatin and carboplatin). As seen in FIGS. 1-4, the activity of all new complexes, except for complex (7), at different concentrations (6.2 µM to 50 µM) is significantly greater than the activity of Pt(II) precursor which is used as a control against human cancer cell lines. These results demonstrate that the cytotoxic activity increases dramatically toward the synthesized complexes of Pt(II) ion coordinated to different inorganic and/or organic ligands, which is consistent with previous reports from the literature [W. Hernandez, J. Paz, A. Vaisberg, E. Spodine, R. Richter, and L. Beyer, Bioinorganic Chemistry and Applications, doi:10.1155/2008/690952, (2008); Shailendr, N. Bharti, F. Naqvi, A. Azam, Bioorganic & Medicinal Chemistry Letters., 13 (2003) 689-692; W. Hernandez, E. Spodine, L. Beyer, et al., Bioinorganic Chemistry and Applications, vol. 3, no. 3-4, pp. 299-316, 2005; M. S. Bakkar, M. Y. Siddiqi, and M. S. Monshi, Synthesis and Reactivity in Inorganic, Metal-Organic, and Nano-Metal Chemistry, vol. 33, no. 7, 1157-1169, 2003—each incorporated herein by reference in its entirety]. In vitro cytotoxic of complexes (1)-(3), (5) and (6) against Hela (human cervical cancer) cell line is exceptionally good and 5-7 times better than cisplatin and 13-20 times better than carboplatin, as shown in Table 5. All synthesized complexes have shown high anticancer activity against all four human cancer cell lines and complex (6) has the highest activity against MCF-7 (human breast cancer) cell line with $IC_{50}$ value 1.23±0.34 μM. The cytotoxicity of complex (6) against the rest of cancer cell lines is also better than cisplatin and carboplatin. Overall, complex (3) was found to be the most effective against all cancer cell lines. These results show better in vitro cytotoxicity of new complexes against a particular cancer cell lines and make them strong candidates as a potential anticancer agents for drug discovery.

TABLE 5

$IC_{50}$ values in (μM) of prepared compounds (1)-(7), Pt(II) precursor, cisplatin and carboplatin against four human tumor cell lines.

| Compounds | HeLa | A549 | MCF7 | HCT15 |
|---|---|---|---|---|
| | $IC_{50}$ ± SEM[a] (standard error measurements) | | | |
| Cisplatin | 19.20 ± 1.81 | 41.67 ± 1.17 | 22.40 ± 1.37 | 29.67 ± 2.35 |
| Carboplatin | 56.47 ± 2.23 | 71.20 ± 2.84 | 55.63 ± 2.53 | 63.90 ± 2.25 |
| Pt(II) precursor | 45.80 ± 2.33 | 55.60 ± 2.53 | 59.77 ± 2.15 | 39.13 ± 1.98 |
| (1) | 1.40 ± 0.29 | 3.50 ± 0.74 | 4.67 ± 1.05 | 7.03 ± 1.04 |
| (2) | 1.83 ± 0.26 | 3.93 ± 0.47 | 2.63 ± 0.88 | 8.60 ± 0.93 |
| (3) | 1.50 ± 0.21 | 2.37 ± 0.29 | 3.77 ± 0.61 | 4.23 ± 0.73 |
| (4) | 9.90 ± 1.65 | 12.63 ± 1.09 | 13.50 ± 1.36 | 16.07 ± 1.13 |
| (5) | 2.23 ± 0.52 | 4.50 ± 0.78 | 4.73 ± 0.95 | 6.87 ± 1.07 |
| (6) | 1.83 ± 0.35 | 3.60 ± 0.72 | 1.23 ± 0.34 | 5.70 ± 0.91 |
| (7) | 17.27 ± 1.34 | 27.73 ± 1.48 | 22.33 ± 1.35 | 37.10 ± 1.86 |

[a]Errors are standard deviations determined from at least three independent experiments.

The experimental results in Table 5 are presented as micro-mole concentration of 50% cell growth inhibition ($IC_{50}$) of each drugs. The MTT assay was performed in three independent experiments, each in triplicate. The cancer cell lines used are HeLa (human cervical cancer), A549 (human lung cancer), MCF-7 (human breast cancer) and HCT15 (human colon cancer) cell lines.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A platinum(II) complex of Formula I, Formula II, Formula III, Formula IV, Formula V or Formula VI:

Formula I

Formula II

Formula III

Formula IV

Formula V

Formula VI or a pharmaceutically acceptable salt, tautomer, ester, or solvate thereof; where $R_1$-$R_{18}$ are each independently a hydrogen atom, a halogen atom, an optionally substituted $C_1$-$C_3$ alkyl group, an optionally substituted $C_1$-$C_3$ alkoxy group, an optionally substituted $C_2$-$C_3$ alkenyl group or an optionally substituted $C_2$-$C_3$ alkynyl group.

2. The platinum(II) complex of claim 1, of Formula I, Formula III or Formula V.

3. The platinum(II) complex of claim 1, where $R_1$-$R_{18}$ are each independently a hydrogen, a halogen, an optionally substituted $C_1$-$C_2$ alkyl group, an optionally substituted $C_1$-$C_2$ alkoxy group, an optionally substituted $C_2$ alkenyl group or an optionally substituted $C_2$ alkynyl group.

4. The platinum(II) complex of claim 1, where:
   $R_1$-$R_6$ are each an ethyl group;
   $R_7$-$R_{10}$ are each a hydrogen, a methyl group or an ethyl group; and
   $R_{11}$-$R_{18}$ are each a hydrogen.

5. The platinum(II) complex of claim 1, wherein the platinum(II) complex is
   cis-bis(triethylphosphine)di(imidazolidine-2-thione)platinum(II);
   cis-bis(triethylphosphine)di(1-methylimidazolidine-2-thione)platinum(II);
   cis-bis(triethylphosphine)di(1,3-dimethylimidazolidine-2-thione)platinum(II);
   cis-bis(triethylphosphine)di(1,3-diethylimidazolidine-2-thione)platinum(II);
   cis-bis(triethylphosphine)di(tetrahydropyrine-2(1H)-thione)platinum(II);
   cis-bis(triethylphosphine)di(1-methyltetrahydropyrimidine-2(1H)-thione)platinum(II); or
   cis-bis(triethylphosphine)di(1,3-diazepane-thione)platinum(II).

6. The platinum(II) complex of claim 1, further comprising one or more pharmaceutically acceptable anions.

7. The platinum(II) complex of claim 6, wherein the one or more pharmaceutically acceptable anions are chloride.

8. A pharmaceutical composition, comprising:
   at least one of the platinum(II) complex of claim 1, a pharmaceutically acceptable salt, tautomer, ester, and solvate thereof; and
   one or more pharmaceutically acceptable carriers.

9. The pharmaceutical composition of claim 8, further comprising one or more other active pharmaceutical agents.

10. The pharmaceutical composition of claim 8, further comprising one or more on-active ingredients.

11. The pharmaceutical composition of claim 8, wherein the composition is in solid, semi-solid or liquid dosage forms.

12. The pharmaceutical composition of claim 8, wherein the composition is formulated for one or more modes of administration selected from the group consisting of oral administration, systemic administration, parenteral administration, inhalation spray, infusion, rectal administration, topical administration, intravesical administration, intradermal administration, transdermal administration subcutaneous administration, intramuscular administration, intralesional administration, intracranial administration, intrapulmonal administration, intracardial administration, intrastemal administration and sublingual administration.

13. A method for decreasing the viability of one or more cancer cells, comprising:
    contacting the cancer cells with a composition comprising a cytotoxically effective amount of the platinum(II) complex of claim 1 or a pharmaceutically acceptable salt, tautomer, ester, or solvate thereof,
    wherein the cancer cells are selected from the group consisting of lung cancer cells, breast cancer cells, colon cancer cells and cervical cancer cells, and
    the cell viability is measured with an MTT assay.

14. The method of claim 13, further comprising contacting the cancer cells with a cytotoxically effective amount of one or more cytotoxic agents prior to, simultaneously with or after contacting of the composition.

15. A method for inducing apoptosis in one or more cancer cells, comprising:
    contacting the cancer cells with the platinum(II) complex of claim 1 or a pharmaceutically acceptable salt, tautomer, ester, or solvate thereof,
    wherein the cancer cells are selected from the group consisting of lung cancer cells, breast cancer cells, colon cancer cells and cervical cancer cells.

16. The method of claim 15, wherein the platinum(II) complex has a concentration of 1-100 μM.

* * * * *